(12) United States Patent
Marks et al.

(10) Patent No.: US 9,335,281 B2
(45) Date of Patent: May 10, 2016

(54) APPARATUS FOR CODED APERTURE X-RAY SCATTER IMAGING AND METHOD THEREFOR

(71) Applicant: Duke University, Durham, NC (US)

(72) Inventors: Daniel Marks, Durham, NC (US); David Jones Brady, Durham, NC (US)

(73) Assignee: Duke University, Durham, NC (US)

( * ) Notice: Subject to any disclaimer, the term of this patent is extended or adjusted under 35 U.S.C. 154(b) by 71 days.

(21) Appl. No.: 14/350,073

(22) PCT Filed: Oct. 4, 2012

(86) PCT No.: PCT/US2012/058744
§ 371 (c)(1),
(2) Date: Apr. 7, 2014

(87) PCT Pub. No.: WO2013/103408
PCT Pub. Date: Jul. 11, 2013

(65) Prior Publication Data
US 2014/0247920 A1    Sep. 4, 2014

Related U.S. Application Data

(60) Provisional application No. 61/663,353, filed on Jun. 22, 2012, provisional application No. 61/544,332, filed on Oct. 7, 2011.

(51) Int. Cl.
*G01N 23/201* (2006.01)
*G01N 23/20* (2006.01)

(52) U.S. Cl.
CPC ........ *G01N 23/201* (2013.01); *G01N 23/20008* (2013.01); *G21K 2207/005* (2013.01)

(58) Field of Classification Search
CPC .......... G01N 23/201; G01N 23/20008; G21K 2207/005

USPC ..................................................... 378/70–90
See application file for complete search history.

(56) References Cited

U.S. PATENT DOCUMENTS

| 5,940,468 | A | 8/1999 | Huang et al. |
| 6,205,195 | B1 * | 3/2001 | Lanza ........................... 376/157 |
| 6,392,235 | B1 | 5/2002 | Barrett et al. |
| 7,283,231 | B2 | 10/2007 | Brady et al. |
| 7,427,932 | B2 | 9/2008 | Brady et al. |
| 7,432,843 | B2 | 10/2008 | Brady et al. |
| 7,463,174 | B2 | 12/2008 | Brady et al. |
| 7,463,179 | B2 | 12/2008 | Brady et al. |
| 7,583,783 | B2 | 9/2009 | Harding |
| 7,616,306 | B2 | 11/2009 | Brady et al. |
| 7,623,614 | B2 | 11/2009 | Shefsky |
| 7,835,495 | B2 | 11/2010 | Harding |
| 7,912,173 | B2 | 3/2011 | Brady |

(Continued)

OTHER PUBLICATIONS

Athina Nickitas-Etienne, "Related International Application No. PCT/US2012/058744", "International Report of Patentability", Apr. 17, 2014, Publisher: PCT.

(Continued)

*Primary Examiner* — Courtney Thomas
(74) *Attorney, Agent, or Firm* — Kaplan Breyer Schwarz & Ottesen, LLP

(57) ABSTRACT

A system and method for producing images of the structure and composition of an object based on measurements of the low-angle x-ray diffraction properties of the object. The imaging system includes a coded aperture that encodes spatial and spectral features onto radiation scattered from image points within the object. The radiation is detected at a two-dimensional array of detectors, whose output is deconvolved and processed to estimate a three-dimensional image having molecular specificity.

29 Claims, 9 Drawing Sheets

(56) References Cited

U.S. PATENT DOCUMENTS 8,149,400 B2     4/2012    Brady et al.
2011/0019068 A1*   1/2011    Chiu ............................. 348/349

OTHER PUBLICATIONS

Officer: Shane Thomas, "Parent International Application No. PCT/US2012/058744", "International Search Report & Written Opinion", Jun. 17, 2013, Publisher: PCT, Published in: US.

MacCabe, et al., "Pencil beam coded aperture x-ray scatter imaging", "Optics Express", Jul. 16, 2012, pp. 16310-16320, vol. 20, No. 15, Publisher: OSA, Published in: US.

Mrozack, et al., "Coded aperture spectroscopy with denoising through sparsity", "Optics Express", Jan. 16, 2012, pp. 2297-2309, vol. 20, No. 2, Publisher: OSA, Published in: US.

William Hadley Richardson, "Bayesian-Based Iterative Method of Image Restoration", Jan. 1972, pp. 55-59, vol. 62, No. 1, Publisher: Journal of the Optical Society of America, Published in: US.

* cited by examiner

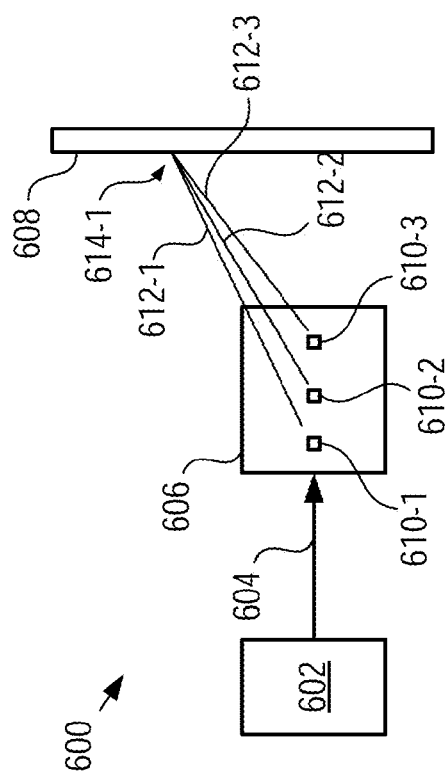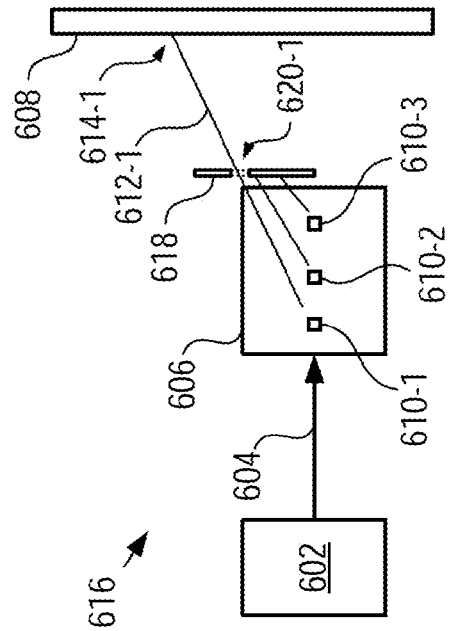

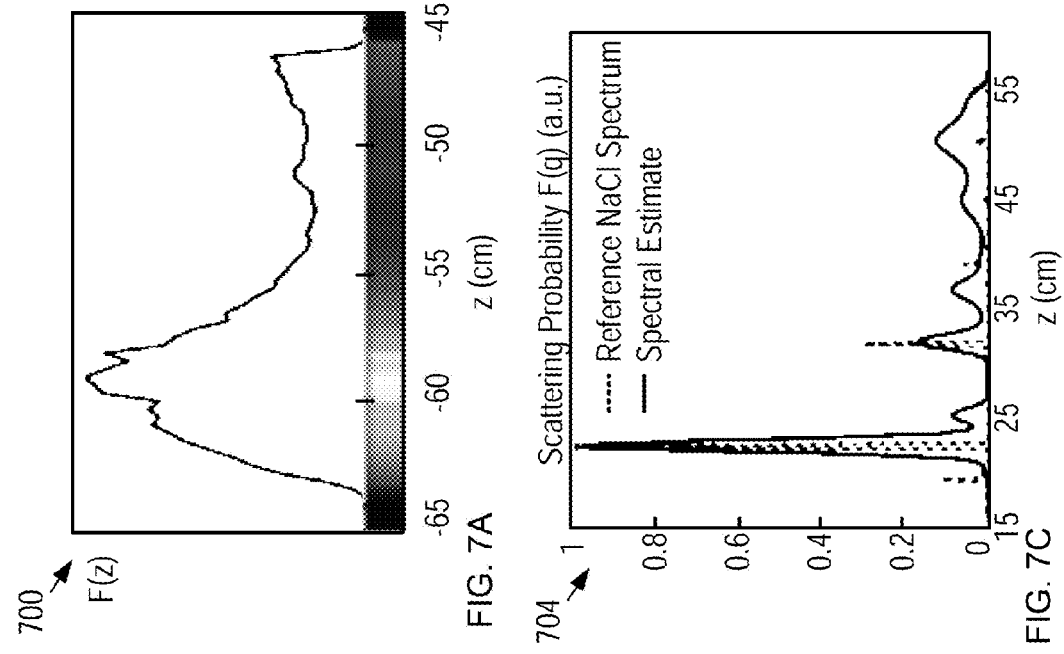

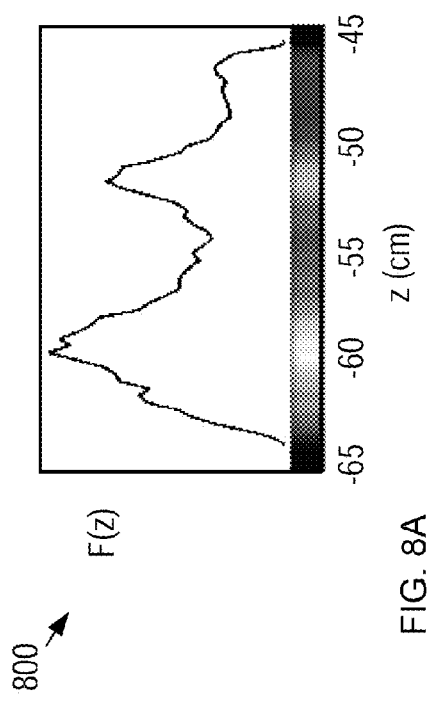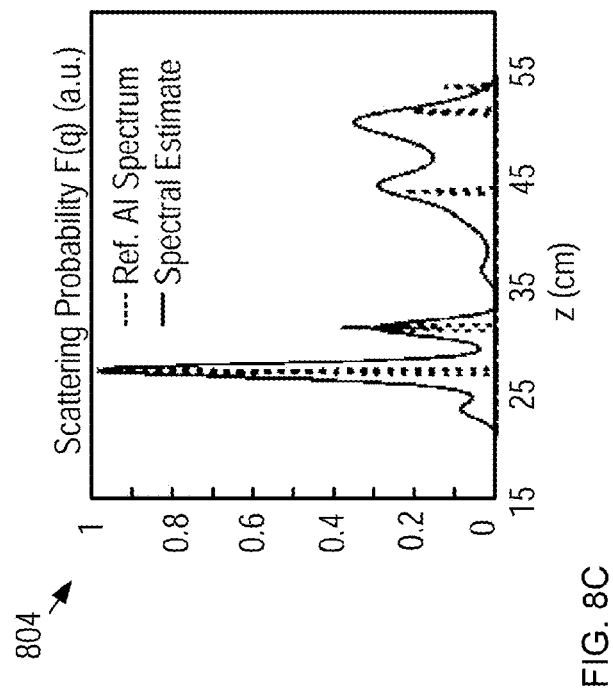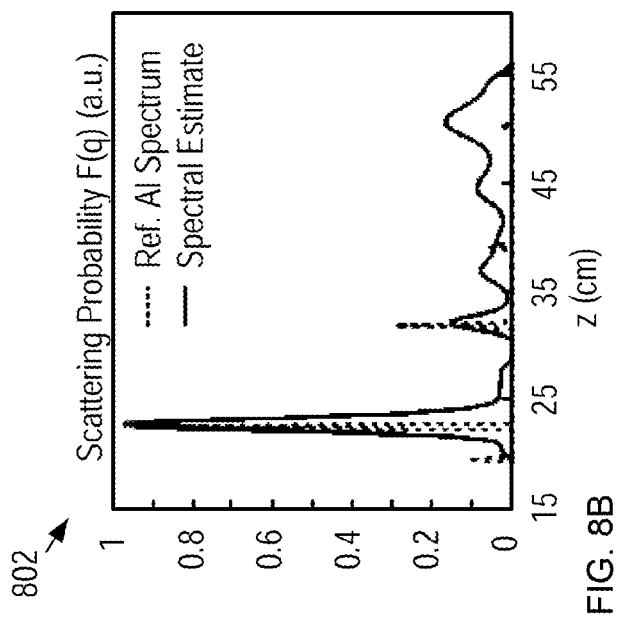
FIG. 8A
FIG. 8B
FIG. 8C

APPARATUS FOR CODED APERTURE X-RAY SCATTER IMAGING AND METHOD THEREFOR

CROSS REFERENCE TO RELATED APPLICATIONS

This application claims the benefit of U.S. Provisional Application Ser. No. 61/544,332, filed Oct. 7, 2011, entitled "Apparatus for Coded Aperture x-ray Scatter Imaging and Methods of Use," and U.S. Provisional Application Ser. No. 61/663,353, filed Jun. 22, 2012, entitled "Apparatus for Coded Aperture x-ray Scatter Imaging and Methods of Use," each of which is incorporated by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING FEDERALLY SPONSORED RESEARCH

This invention was made with Government support under HSHQDC-11-C-0083 awarded by the Department of Homeland Security. The Government has certain rights in the invention.

FIELD OF THE INVENTION

The present invention relates to imaging in general, and, more particularly, to x-ray scatter imaging.

BACKGROUND OF THE INVENTION

The ability to non-invasively image the molecular composition of an object is desirable in a number of application areas, such as medical imaging, security, structural integrity verification, and homeland defense. While x-ray imaging is the most effective strategy for tomographic imaging in such applications, conventional x-ray systems are not sensitive to molecular composition. X-rays interact with materials via photoelectric absorption, Compton scatter, coherent (Bragg) scatter and fluorescence. Conventional x-ray imaging primarily measures absorption and Compton scatter; however, only coherent scatter and fluorescence are sensitive to molecular or atomic identity.

A traditional x-ray imaging system detects hard and soft materials by the variation in x-ray transmission through an object. More recently, however, imaging systems based on x-ray scattering by the structure of an object have been developed, such as described in U.S. Pat. No. 7,835,495 entitled "System and Method for X-ray Diffraction Imaging," which discloses a method for x-ray scatter imaging using collimators on each of an array of detector elements. While such approaches give rise to detectors that are sensitive to the direction of x-ray propagation, the use of the collimators severely limits photon efficiency.

Alternative approaches for imaging systems have been developed that employ multiplexed measurements from shaped x-ray beams, such as a fan-shaped beam, to construct x-ray scatter images. Examples of such systems are disclosed in U.S. Pat. No. 7,583,783 entitled "X-ray Computer Tomograph and Method for Examining a Test Piece Using an x-ray Computer Tomograph." Unfortunately, these approaches require multiple exposures and are relatively poorly conditioned for mathematical image estimation.

Backscatter x-ray systems detect a relatively small amount of radiation that reflects from the object and use it to form an image. These systems are particularly attractive for applications where less-destructive examination is required or where only one side of the target is available for examination. The backscatter pattern is dependent on the properties of the material being interrogated, and is good for imaging a wide range of materials. Backscatter x-ray imaging systems include full-body airport scanners, which are currently being used to detect hidden weapons, tools, liquids, narcotics, currency, etc. As with forward scatter, in backscatter systems that rely on collimators rather than coded apertures only a small percentage of the incident radiation is detected. Backscatter x-ray systems require high-power x-ray sources and/or high-sensitivity detectors in order to provide acceptable resolution and signal-to-noise ratio (SNR). Line-scan systems utilizing a fan beam of radiation to inspect an object and a segmented detector to measure radiation transmitted through the object are able to use a higher portion of available source flux; however, they are generally incapable of producing images from backscattered radiation.

Forward-scattering x-ray scatter imaging systems such as those described in U.S. Pat. No. 7,835,495, employ a primary beam of x-ray radiation that is scanned over an object while radiation from elastic (coherent) scattering is monitored by a fixed-position, energy-resolving detector. The detector is located at a small, fixed angle to the direction of propagation of the primary beam. Information about the crystallographic structure of the material of the scattering object is derived from the resultant scatter spectra. This information can then be compared to known scatter spectra in a library of materials of interest to determine if any such materials are included in the object being scanned.

Unfortunately, scanning x-ray systems capture only a small fraction of the radiation directed at the scanned object and are, therefore, highly inefficient. As a result, in order to produce an output signal having sufficiently high SNR, they require either x-ray sources capable of high power to increase the available radiation at the detector, or long exposure times. In either case, this exposes the scanned object to excessive amounts of x-ray radiation, which can be undesirable in many applications.

In addition, conventional x-ray imaging systems typically employ substantially monochromatic radiation or rely on energy discriminating detectors to improve resolution and signal quality. As a result, the total incident photon flux on the object of interest is limited.

Further, while conventional x-ray diffraction imaging approaches might be suitable for interrogating small-size (<1 $cm^2$) areas, their data acquisition time makes it impractical to scan entire bags or parcels. The size limitation arises, in part, from the fact that while energy resolving detectors can discriminate x-ray diffraction orders from different wavelengths, they are quite expensive—particularly in array sizes necessary for high-speed, high-resolution imaging. Improved "fan beam" tomographic imaging systems offer some improvement in detection efficiency; however, these systems require expensive energy-resolving x-ray detectors and/or low-flux low-bandwidth x-ray sources. Still further, these systems are not well suited for scanning arbitrary objects whose composition can vary over a wide range since detection of a constituent material requires some advance knowledge or suspicion of the presence of that material so that its scattering "fingerprint" can be included in the material library.

Computational x-ray tomography, such as is described in U.S. Pat. No. 7,583,783, has been shown capable of producing images that are also based on measurements of the low-angle x-ray diffraction properties of an object. Such systems typically scan a "pencil beam" of x-ray radiation over a series of locations on the object and use computational processing-over many exposures to acquire a diffraction pattern for each scanned location. These diffraction patterns are used to reconstruct a series of images, which represent the coherent-scatter intensity at a series of scatter angles. Coherent-scatter cross-sections of the object can then be generated for each pixel from the sequence of images to develop a tomographic reconstruction of the object.

Like x-ray scatter-imaging systems, however, computed x-ray tomography systems do not efficiently utilize the x-ray energy directed at the scanned object. In addition, the need to develop the tomographic model of the object one cross-section at time leads to an undesirable space-time spectral trade-off.

There remains a need, therefore, for an improved imaging system that noninvasively ascertains the structural and molecular composition of three-dimensional objects at high speed and with relatively lower cost and complexity.

SUMMARY OF THE INVENTION

The present invention enables non-invasive, three-dimensional imaging of the structure and molecular composition of an image point of an object in a single snapshot. Embodiments of the present invention are well suited for use applications including luggage scanning, cargo inspection, explosives detection, and medical imaging. Some embodiments of the present invention are particularly well suited for use in imaging objects whose size scale is 10 centimeters or larger.

Embodiments of the present invention include a coded aperture in an optical path that extends from an x-ray source through an object under text and to a detector array. The coded aperture enables multiplexed measurement of scatter angles, spatial, and spectral information from the object. In some embodiments, the coded aperture is located between the object and the detector. In some embodiments, the coded aperture is located between the source and the object.

In embodiments wherein the object is interrogated by a pencil beam x-ray signal, the inclusion of the coded aperture enables instantaneous and simultaneous measurement of scatter angle and object density versus range (i.e., longitudinal position) along the pencil beam without the loss of throughput inherent to the use of collimation filters at the detector elements, as used in the prior art.

It is an aspect of the present invention that the use of a coded aperture having a code that provides suitable orthogonality versus scale rather than translation affords embodiments of the present invention significant advantage over prior-art x-ray imaging systems. In some embodiments, the code is a periodic code, while in other embodiments, the code is a random code. It is a further aspect of the present invention that periodic or random codes can significantly outperform uniformly redundant arrays.

It is another aspect of the present invention that the use of reference structures or coded apertures in combination with decompressive inference enables instantaneous or reduced time estimation of fan beam or volume scatter signatures, especially joint estimation of momentum transfer spectra and spatial structure.

Imagers in accordance with the present invention include a coded aperture that encodes spatial and spectral features of radiation scattered from image points within an object to efficiently use the flux of polychromatic x-ray photons scattered from the object to form a two- or three-dimensional image with molecular specificity. In some embodiments, a pencil beam of x-ray radiation interrogates a line of image points through the object. The coherent scatter properties of the object can be estimated at each image point along the line by acquiring a single irradiance image at a two-dimensional irradiance detector. By scanning the pencil beam over the transverse extent of the object, a complete volumetric molecular image of the object can be estimated.

An illustrative embodiment of the present invention comprises a source of x-ray radiation, a primary aperture, a coded aperture, and a detector array. The primary aperture receives x-ray radiation from the source and provides a pencil beam of radiation, which is directed at an object to be imaged. The pencil-beam radiation is incident on the object along a central axis. As the radiation interacts with the materials of the object, it is scattered along forward directions, whose angles with respect to the central axis depend upon the molecular structure of the materials. The scattered radiation passes through the coded aperture, which acts as a reference structure that modulates the scattered radiation. The modulated radiation is received at the detector, which comprises an array of irradiance detectors. The modulation of the scattered radiation removes its range/angle ambiguity, thus affording an angular sensitivity to each pixel of the detector array.

In some embodiments, relative transverse motion between the pencil beam and the object is enabled such that the entire transverse extent of the object is interrogated.

In some embodiments, a fan beam of x-ray radiation is used instead of the pencil beam. Such embodiments enable an improved temporal resolution, among other advantages. In some embodiments, a cone beam of radiation is used.

An embodiment of the present invention comprises an x-ray scatter imaging system including: a source operable for interrogating an object with a first signal comprising x-ray radiation; a detector operable for detecting a second signal comprising x-ray radiation scattered from the object, the detector including a two-dimensional array of pixels; and a coded aperture operable for modulating the second signal.

BRIEF DESCRIPTION OF THE DRAWINGS

FIG. 6A depicts a simplified schematic diagram of an x-ray scatter imaging system.

FIG. 6B depicts a schematic diagram of x-ray imaging system 600 with an included pinhole mask.

FIG. 7A depicts a spatial scattering profile for a first test sample interrogated by a pencil beam of x-ray radiation.

FIG. 7B depicts a spatial scattering profile for a second test sample interrogated by the pencil beam of x-ray radiation.

FIG. 7C depicts a momentum transfer profile for the first test sample.

FIG. 7D depicts a momentum transfer profile for the second test sample.

FIG. 8A depicts a spatial scattering profile for both the first and second test sample simultaneously interrogated by a pencil beam of x-ray radiation.

FIG. 8B depicts a momentum transfer profile for the first of two test samples simultaneously interrogated by a pencil beam of x-ray radiation.

FIG. 8C depicts a momentum transfer profile for the second of two test samples simultaneously interrogated by a pencil beam of x-ray radiation.

DETAILED DESCRIPTION

X-ray diffraction occurs when x-rays scatter elastically from the electrons in an object. Coherence between the scattered x-rays leads to interference effects that give rise to distinct diffraction patterns that can provide insight into the atomic-level structure of the particular material under examination.

X-ray diffraction has been routinely used for many years to determine the structure of crystalline materials in applications such as molecular beam epitaxy (MBE), vapor-phase epitaxy (VPE), and atomic-layer epitaxy (ALE), since the diffraction patterns generated are dependent upon the atomic locations within the crystal. Recently, it has also been directed toward medical applications as well, such as determination of bone-mineral content via measurement of low-angle coherent-scatter x-ray diffraction. An estimation of bone-mineral content at a measurement site within a test sample can be made, for example, by generating scatter diagrams and measuring the angles of peak scatter in a test sample and comparing the results to scatter diagrams for control samples having known proportions of adipose tissue and cortical bone. In order to develop an image of the entire test sample, the sample can be scanned through a focal point using a scanning pattern that interrogates a desired arrangement of measurement sites. Unfortunately, this method makes very inefficient use of the x-rays that hit the object; therefore, undesirably high x-ray doses are required. Further, it has been found that matter density and fat content of the material being examined can introduce errors in the bone-mineral-content measurements.

More recently, coherent-scatter computed tomography (CSCT) using a poly-energetic x-ray beam has been proposed as an improvement to low-angle coherent-scatter x-ray diffraction. CSCT has demonstrated an ability to determine the angular-dependent coherent-scatter cross-section for each pixel in a tomographic slice of an object. CSCT has been shown to be effective for measuring bone-mineral content that is independent of material density and fat content.

Figure 1:
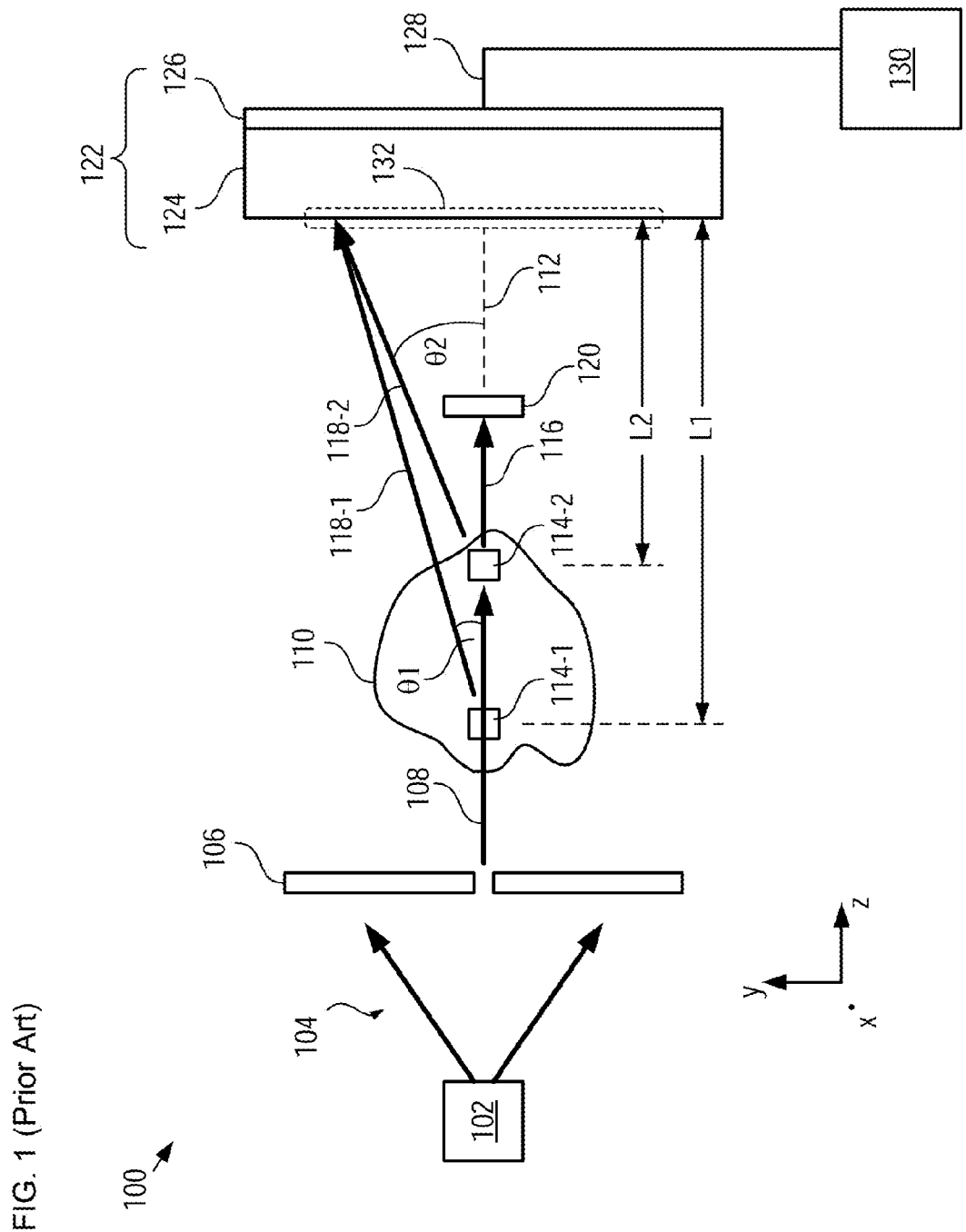
FIG. 1 depicts a schematic diagram of a coherent-scatter computed tomography system in accordance with the prior art.

FIG. 1 depicts a schematic diagram of a CSCT system in accordance with the prior art. System 100 comprises x-ray source 102, collimator 106, blocker 120, detector 122, and processor 128. System 100 is analogous to CSCT systems described by Westmore, et al. in "Tomographic imaging of the angular-dependent coherent-scatter cross section," *Medical Physics*, Vol. 24, pp. 3-10 (1997), and which is incorporated herein by reference.

X-ray source 102 provides poly-energetic x-ray emission 104, which is collimated by collimator 106 to form pencil beam 108.

Object 110 is positioned so that it is interrogated by pencil beam 108 along axis 112, which exposes object elements 114-1 and 114-2 to pencil beam 108. It should be noted that object elements 114-1 and 114-2 are volumetric portions of object 110 that has a finite width, height, and depth. Object 110 is typically positioned, relative to pencil beam 108, by a multi-axis stage capable of translation along the x-axis, y-axis, and z-axis and rotation about each of the x-axis and y-axis.

At each of object elements 114-1 and 114-2, a portion of pencil beam 108 is scattered into transmitted primary beam 116 and scatter radiation. Specifically, object element 114-1 scatters the x-ray radiation into scatter radiation 118-1 at an angle of θ1 to axis 112, and object element 114-2 scatters the x-ray radiation into scatter radiation 118-2 at an angle of θ2 to axis 112. The specific value of the scatter angle of the scatter radiation from each object point depends on its particular material composition.

Blocker 120 is placed in the path of transmitted primary beam 116 to block its transmission to detector 122. Typically, blocker 120 is a lead disc or equivalent.

Each of scatter radiation 118-1 and 118-2 is incident on detector 122 at a point that is based on its scatter angle and distance from detector 122. Specifically, scatter radiation 118-1 is incident on detector 122 at a point based on scatter angle θ1 and distance L1, while scatter radiation 118-2 is incident on detector 122 at a point based on scatter angle θ2 and distance L2. Collectively, scatter radiation 118-1 and 118-2 form scatter image 132 on detector 122. Scatter image 132 is the collective pattern of scatter radiation 118-1 and 118-2 that is incident on detector 122. Detector 122 comprises scintillator 124, which converts x-ray energy into visible light, and focal-plane array 126. Focal-plane array 126 is typically a conventional CCD array that receives the visible light from scintillator 124.

Detector 122 provides output signal 128, which is based on scatter image 132, to processor 130. Processor 130 then forms a diffraction pattern based on output signal 128.

Unfortunately, system 100 has several drawbacks. Since each of object elements 114-1 and 114-2 has finite length along the z-axis, and is not necessarily of uniform composition throughout, the diffraction pattern formed from scatter radiation 118-1 and 118-2 is affected by the point within the object elements from which it scatters, the material composition at that point, and the angle of incidence of pencil beam 108 on it. As a result, interrogation of an image point by a pencil beam directed at a single angle results in a lack of clarity about the composition of that image point. For clarity in FIG. 1, scatter radiation 118-1 and 118-2 is depicted as a single ray of radiation; however, one skilled in the art will recognize that the scatter radiation is actually incident on detector 122 at a plurality of points whose incidence pattern is indicative of the constituent materials at its respective object element.

As depicted in FIG. 1, the scatter radiation from more than one object element along axis 112 can hit detector 122 at the same point, confounding the measurement results. In order to overcome these limitations, object 110 is rotated over a range of angles such that pencil beam 108 intersects each object element at a plurality of beam angles. A typical scan, for example, includes diffraction patterns generated at 64 beam angles at each of 64 object elements within the volume of object 110. For 64 object elements and 64 beam angles, this results in the generation of a total of 4096 diffraction patterns. Since the generation of each diffraction pattern requires a significant scan time, the total amount of time to scan object 110 can become prohibitive.

Further, at each object element and beam angle, processor 130 receives output signal 128 from detector 122. From this data, processor 130 reconstructs sixteen tomographic images that display the coherent scatter intensity at sixteen different scatter angles.

It is an aspect of the present invention that the application of coded-aperture snapshot imaging concepts to x-ray scatter imaging can give rise to significant advantages over prior-art x-ray imaging systems. Such coded-aperture x-ray scatter-imaging systems can implement compressive snapshot tomography of pencil, fan, and volume data by encoding separable code structures of diverse range and scatter signals.

The present invention applies compressive tomographic imaging techniques to an imaging system such that range imaging of an object under test is enabled. Compressive tomographic imaging, as used herein, is a technique wherein the radiation emanating from each of a plurality of planes of the object under test is encoded via a coded aperture. The radiation from all of the planes is received simultaneously and object reconstruction strategies are applied to decode each of the planes thereby yielding a "tomographic slice" of the object information. Compressive snapshot imaging, as applied to transverse imaging of the spectral properties of an object field, is described in U.S. Pat. No. 8,149,400 entitled "Coded Aperture Snapshot Spectral Imager and Method Therefor," which is incorporated herein by reference. It should be noted that, although the present invention employs object reconstruction strategies that are mathematically similar to strategies disclosed in U.S. Pat. No. 8,149,400, reconstruction strategies in accordance with the present invention operate on novel physical structures. In particular, the present invention enables simultaneous range and scatter angle/momentum imaging, range, cross range and scatter, volumetric imaging or volumetric and scatter imaging.

While coded apertures have been applied to two-dimensional x-ray imaging in the past, their application in tomographic systems has been limited. The previous state-of-the-art is illustrated in U.S. Pat. No. 6,392,235, entitled "Coded-aperture System for Planar Imaging of Volumetric Sources," which discloses a method combining two-dimensional transverse imaging with longitudinal displacement of the coded aperture relative to the target to obtain three-dimensional data. This approach is both mathematically poorly posed and continues the traditional space-time trade-off.

In contrast, the present invention continues an alternative, natively tomographic approach of multi-dimensional tomographic coding, such as is disclosed in U.S. Pat. No. 7,912,173, entitled "Reference Structures and Reference Structure Enhanced Tomography." This patent introduces the idea of compressive tomographic imaging, under which prior constraints are combined with measurements to enable estimation of a number of voxels that is greater than the number of measurement. Further, in tomographic systems, it enables estimation of objects embedded in higher dimension than the measurements such as, for example, estimation of two-dimensional, three-dimensional or four-dimensional tomographic volumes from measurements on one-dimensional lines or two-dimensional surfaces. This eliminates or reduces the traditional space-time trade-off. Similar compressive measurement strategies are also disclosed in greater detail in U.S. Pat. Nos. 7,616,306, 7,463,179, 7,463,174, 7,432,843, 7,427,932, and 7,283,231.

It should be noted, however, that none of the methods disclosed in the prior art, including U.S. Pat. Nos. 7,912,173, 7,616,306, 7,463,179, 7,463,174, 7,432,843, 7,427,932, and 7,283,231, enable recovery of range and scatter angle information about one or more object elements, such as enabled by the present invention. As a result, as described below, the present invention affords significant advantage over these methods by providing molecular and/or atomic information of an object element and thus information about the material composition of an object under test.

Figure 2:
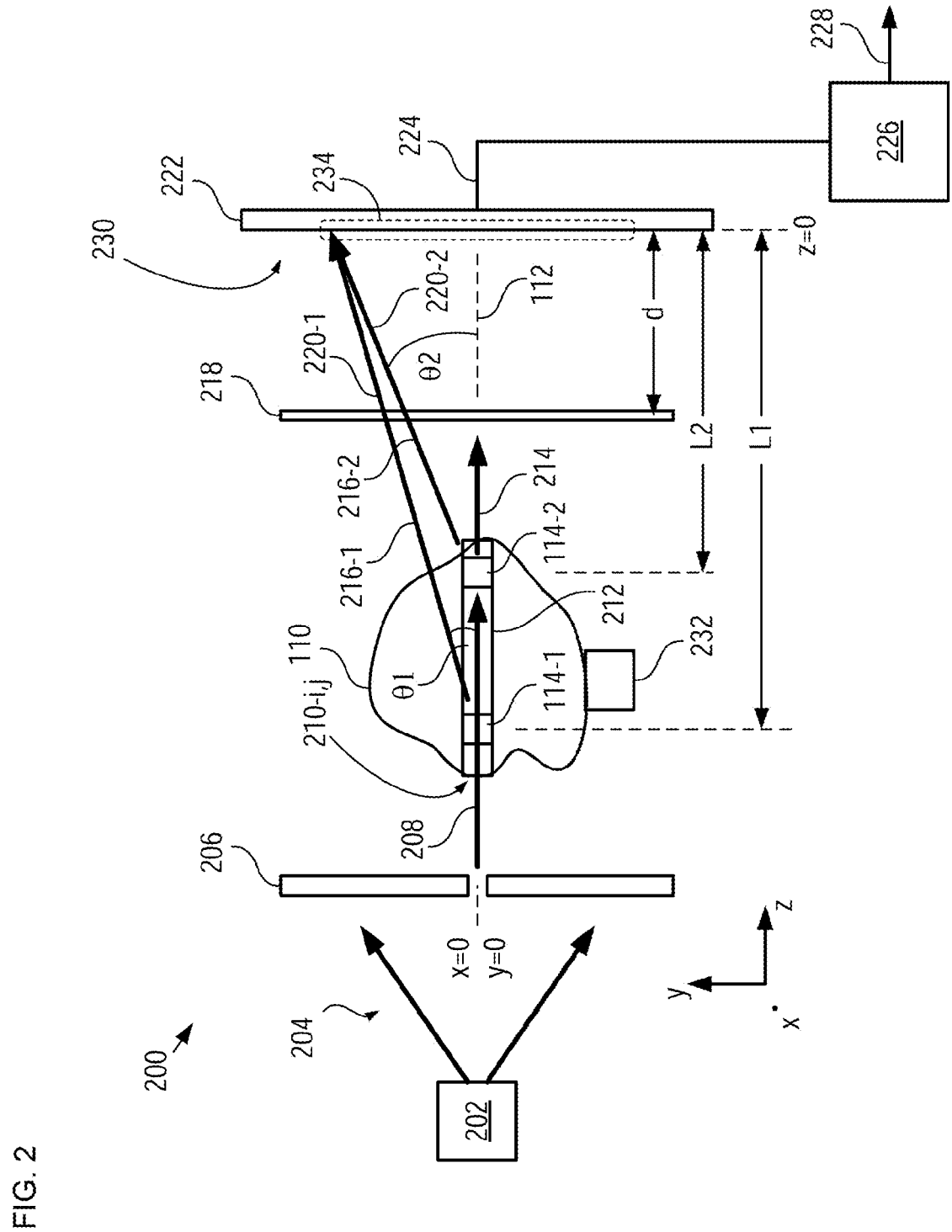
FIG. 2 depicts a schematic diagram of a portion of a coded-aperture x-ray scatter imaging system in accordance with an illustrative embodiment of the present invention.

FIG. 2 depicts a schematic diagram of a portion of a coded-aperture x-ray scatter imaging system in accordance with an illustrative embodiment of the present invention. System 200 comprises source 202, primary aperture 206, coded aperture 218, detector 222, processor 226, and stage 232. System 200 is analogous to system 100, but with the addition of coded aperture 210.

Figure 3:
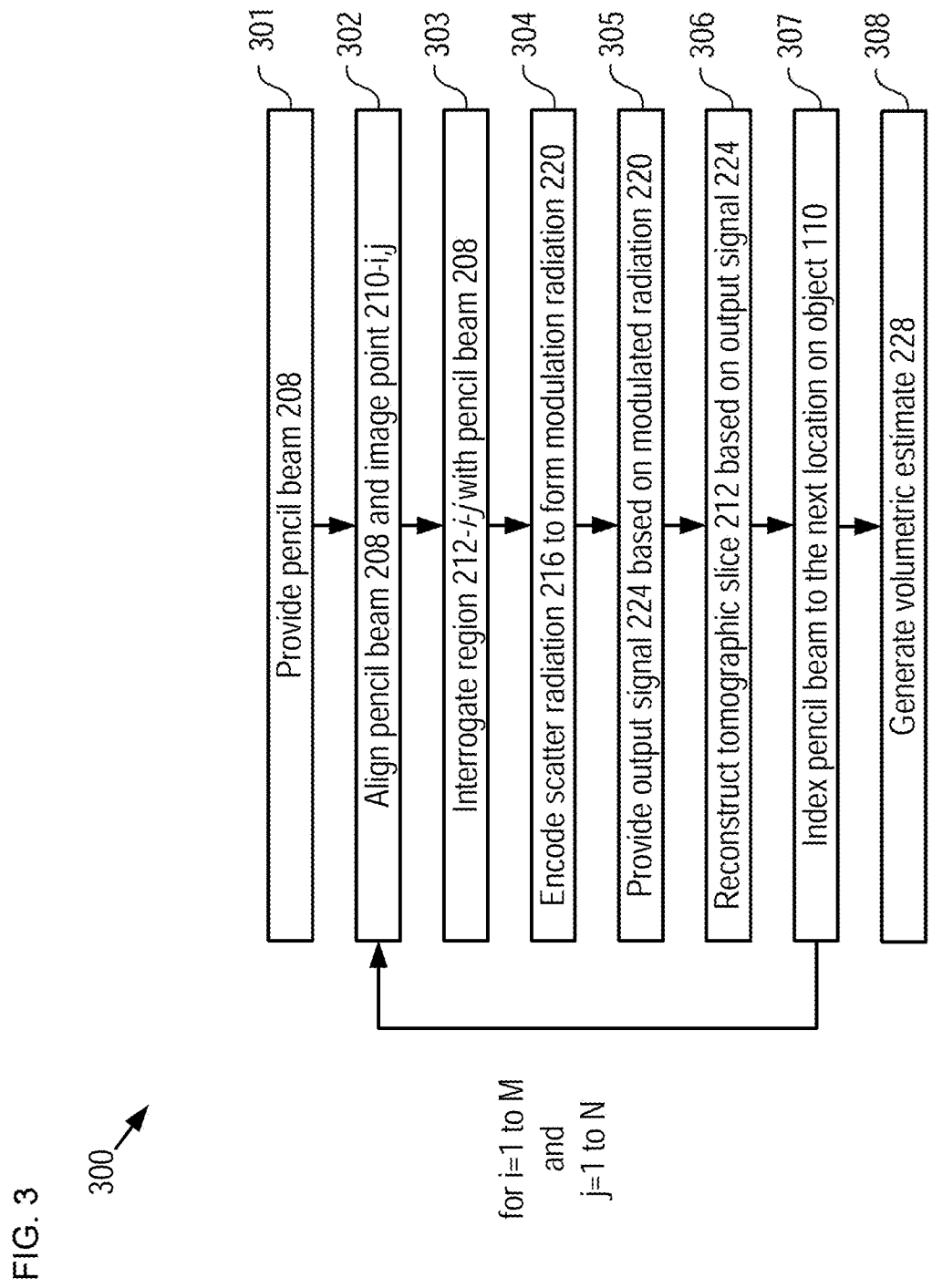
FIG. 3 depicts operations of a method suitable for generating a three-dimensional estimation of the structure and composition of an object in accordance with the illustrative embodiment of the present invention.

FIG. 3 depicts operations of a method suitable for generating a three-dimensional estimation of the structure and composition of an object in accordance with the illustrative embodiment of the present invention. Method 300 begins with operation 301, wherein pencil beam 208 is provided. Systems and methods in accordance with the present invention are disclosed by K. MacCabe, et al., in "Pencil beam coded aperture x-ray scatter imaging," *Optics Express*, Vol. 20, (2012), pp. 16310-16320, which is incorporated herein by reference.

Conventional x-ray source 202 emits poly-energetic x-ray emission 204. To improve the specificity with which material can be classified by system 200, the spectrum of x-ray emission 204 is filtered by a tungsten filter to limit it to an energy passband that ranges from approximately 30 keV to the tungsten K-edge of approximately 69.5 keV. After it has been spectrally shaped, x-ray emission 204 is received by primary aperture 206. In some embodiments, the radiation of pencil beam 208 includes one or more sharp spectral features. It is an aspect of the present invention that the inclusion of sharp spectral features in the output spectrum of source 202 can enable improved accuracy and resolution for system 200.

Primary aperture 206 is a conventional x-ray spatial filter, such as pinhole aperture, which forms a barrier to x-ray emission 204 propagating along directions other than those substantially aligned with axis 232. As a result, primary aperture 206 passes only a substantially parallel bundle of x-rays that collectively define pencil beam 208. In some embodiments, primary aperture 206 is other than a pinhole aperture. In some embodiments, primary aperture enables radiation having a shape other than a pencil beam to pass through and proceed toward object 110, such as a fan-shaped beam or a cone-shaped beam.

At operation 302, pencil beam 208 is aligned with image point 210-$i$-$j$, where i is a number within the range of 1 to M, and j is an integer within the range of 1 to N. Image points 201-$i$-$j$ collectively define a two-dimensional array of image points having M columns along the x-direction and N rows along the y-direction. The values of M and N are based on the cross-sectional area of pencil beam 208 and the lateral extent of object 110 along each of the x- and y-direction. The values of M and N are selected to provide a lateral image resolution suitable for the application for which the use of system 200 is intended.

At operation 303, region 212-$i$-$j$ is interrogated with pencil beam 208. Pencil beam 208 interacts with object elements 114-1 and 114-2 in region 212-$i$-$j$ to scatter pencil beam 208 into transmitted primary beam 214 and scatter radiation 216-1 and 216-2 (referred to, collectively, as scatter radiation 216), which is scattered in the forward direction (with respect to the propagation of pencil beam 208. Scatter radiation 216-1 and 216-2 are analogous to scatter radiation 116-1 and 116-2, and scatter at angles within the range of $\theta 1$ to $\theta 2$, respectively, with respect to the transmitted primary beam 214, based on the material composition of object elements 114-1 and 114-2, as described above and with respect to FIG. 1.

One skilled in the art will recognize that many more than two scatter radiation signals are generated by the interrogation of region 212-$i$-$j$ with pencil beam 208; however, for the purposes of clarity in this discussion, only two scatter radiation signals (i.e., scatter radiation 216-1 and 216-2) are described.

At operation 304, scatter radiation 216-1 and 216-2 are encoded with sampling structure defined by the spatial features of coded aperture 218 to define modulated radiation 220-1 and 220-2, respectively (referred to, collectively, as modulated radiation 220).

Figure 4:
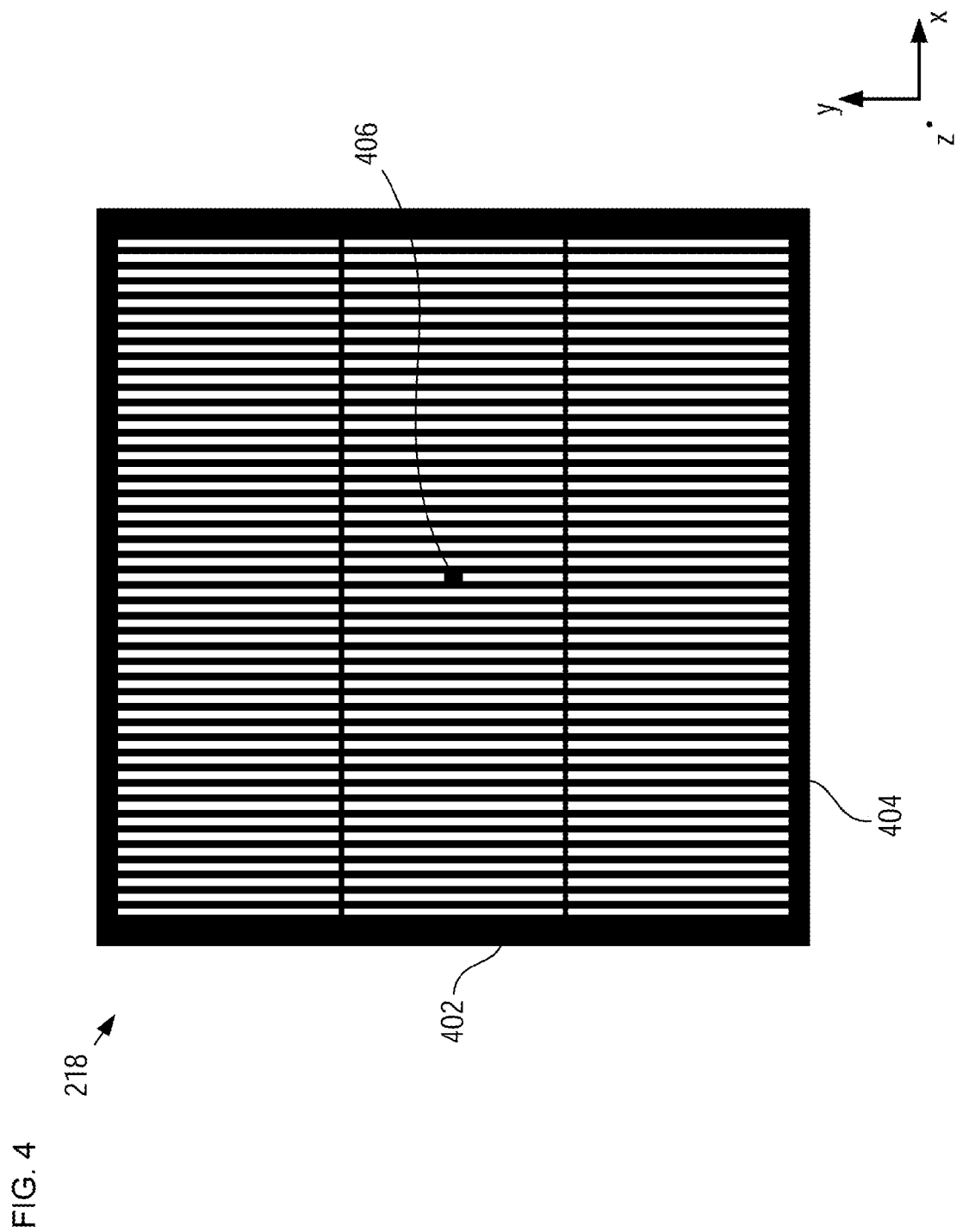
FIG. 4 depicts a schematic drawing of a region of a coded aperture in accordance with the illustrative embodiment of the present invention.

FIG. 4 depicts a schematic drawing of a region of a coded aperture in accordance with the illustrative embodiment of the present invention. Coded aperture 218 comprises frame 402, apertures 404, and blocker 406. In contrast with previous art, coded aperture 218 includes a code (i.e., an arrangement of apertures 404) that is periodic. As a result, aperture 218 enables separable estimation of object density and scatter angle versus range (which is encoded as magnification).

Frame 402 is a lead sheet whose thickness is suitable for blocking transmission of scatter radiation and sufficient mechanical strength to avoid warping or sagging under its own weight when oriented in the x-y plane.

Apertures 404 are openings having a width and height suitable for encoding a spatial code onto scatter radiation 216-1 and 216-2. Apertures 404 are arranged in an arrangement that is periodic in each of the x- and y-dimensions. Apertures 404 are formed in frame 202 using any conventional means, such as milling, drilling, grinding, etching, and the like. In some embodiments, coded aperture 218 is formed via a conventional molding process, such as injection molding, casting, and the like. In some embodiments, apertures 404 are periodic in only one of the x- and y-dimensions. In some embodiments, apertures 404 are not periodic.

The dimensions of frame 402 and the width, height, number, and spacing of apertures 404 are matters of design preference and depend upon the application for which system 200 is intended. For exemplary purposes only, frame 402 is approximately 25 mm×25 mm and has a thickness of approximately 6 mm and includes a 45×3 array of apertures 404. Each of apertures 404 has a width of approximately 0.45 cm and a height of approximately 7.5 mm.

For an isotropic material, scatter radiation 216 has circular symmetry about axis 112. As a result, the same scatter radiation is available at detector 222 multiple times. In some embodiments, therefore, coded aperture 218 includes an aperture pattern that is not circularly symmetric about its center (e.g., a spiral-shaped aperture), which offers an advantage because it enables multiple measurements of the circularly symmetric scatter radiation in a single snapshot.

In some embodiments, coded aperture 218 includes a mask having a pattern of x-ray absorbing material that covers about 50% of its surface area.

It will be clear to one skilled in the art, after reading this Specification, that the pattern of coded aperture 218 is a matter of design choice based on the particular class of objects to be scanned.

Blocker 406 is analogous to blocker 120, as described above. Blocker 406 is a feature located substantially in the center of coded aperture 218. When coded aperture 218 is aligned in system 200, blocker 406 is located so as to block transmitted primary beam 214 from passing to detector 222. The size of blocker 406 is a matter of design. For exemplary purposes, however, blocker 406 has a substantially square shape of approximately 0.5 cm per side. In some embodiments, blocker 406 has a shape other than square.

In some embodiments, coded aperture 218 includes fine structural features. It is an aspect of the present invention that the resolution of the estimation of the composition (i.e., spatial estimation and momentum transfer) for region 212-$i$-$j$ can be improved by improving the spatial resolution of the features in the coded aperture.

At operation 305, detector 222 receives modulated image 234 and provides output signal 224. Modulated image 234 is the collective pattern formed by modulated radiation 220-1 and 220-2 (referred to, collectively, as modulated radiation 220) as it is incident on detector 222.

Detector 222 is a two dimensional array of amorphous-silicon indirect cesium iodide x-ray detectors 230. The lateral extent and position, relative to source 202 and object 110, of detector 222 is suitable for receiving the complete diffraction pattern of modulated radiation 220. For exemplary purposes, detector 222 is a 40 cm×30 cm element that includes a 2048× 1536 array of 0.194 micron-size detectors 230. Detector 222 is located at a distance from source 202 of approximately 201 cm. In this example, the separation between coded aperture 218 and detector 222 is approximately 21 cm. One skilled in the art will recognize, after reading this specification, that amorphous-silicon indirect cesium iodide x-ray detectors represent only one suitable type of detector element suitable for use in detector 222. Further, one skilled in the art will recognize that detector 222 can include any practical number and arrangement of detectors 230.

Although system 200 is a forward-scatter imaging system, it will be clear to one skilled in the art, after reading this Specification, how to specify, make, and use alternative embodiments that image an object based on back-scattered x-ray radiation or side-scattered x-ray radiation.

Further, although the illustrative embodiment comprises a system for forming an image based on modulated scattered x-ray radiation from an object, it will be clear to one skilled in the art, after reading this Specification, how to specify, make, and use alternative embodiments of the present invention that form images based on coded-aperture-modulated radiation other than scattered x-ray radiation, such as modulated fluorescence signals, and the like.

Figure 5:
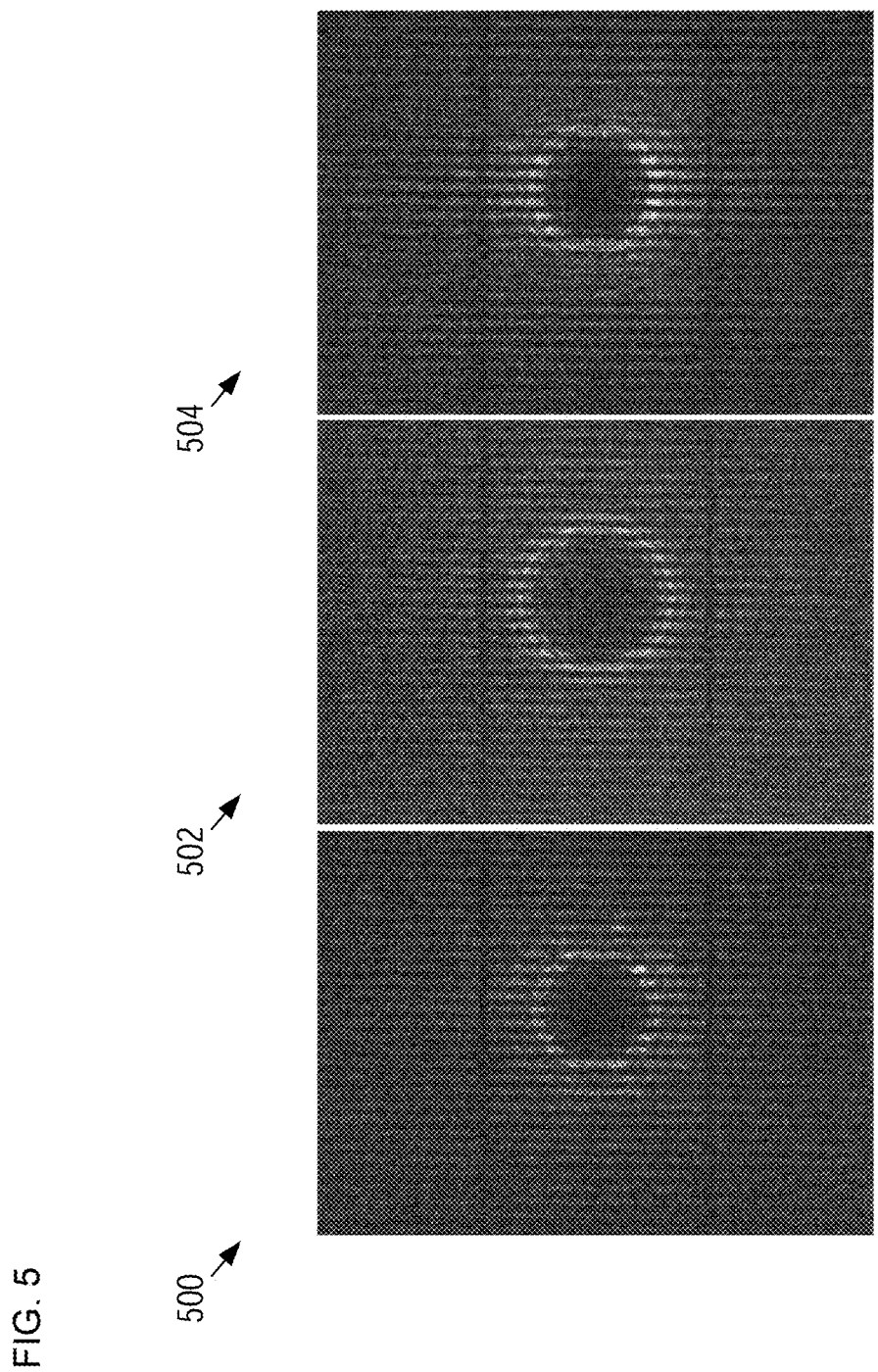
FIG. 5 depicts diffraction images acquired with an imaging system in accordance with the illustrative embodiment of the present invention.

FIG. 5 depicts modulated images acquired with an imaging system in accordance with the illustrative embodiment of the present invention. Image 500 is a modulated image of the modulated radiation obtained from interrogation by pencil beam 208 of a sample of sodium chloride located at a position approximately 60.2 cm from detector 222.

Image 502 is a modulated image of the modulated radiation obtained from interrogation by pencil beam 208 of a sample of aluminum located at a position approximately 60.2 cm from detector 222.

Image 504 is a modulated image of the modulated radiation obtained from interrogation by pencil beam 208 of a sample of sodium chloride located at a position approximately 60.2 cm from detector 222 and a sample of aluminum located at a position approximately 52.6 cm from detector 222.

The insertion of coded aperture 218 between object 110 and detector 222 enables each irradiance pixel of detector 222 to operate as a radiance pixel. This occurs because coded aperture 218 makes each irradiance pixel of the detector sensitive to x-rays arriving from only a limited set of ray directions (i.e., imparts angular sensitivity on the pixel).

Irradiance-to-Radiance Conversion Using Pinholes and Coded Apertures

Coded aperture 218 enables discrimination of scatter radiation emanating from individual object elements 114 by providing a means of converting irradiance into radiance. The advantages afforded embodiments of the present invention by the inclusion of coded aperture 218 in an x-ray scatter imaging system can be readily understood by analogy to the operation of a series of measurements made with a pinhole aperture, as provided here.

FIG. 6A depicts a simplified schematic diagram of an x-ray scatter imaging system. System 600 comprises source 602, object 606, and detector 608.

Source 602 interrogates object 606 with pencil beam of x-ray radiation 604, which gives rise to scatter radiation 612-1, 612-2, and 612-3 from object elements 610-1, 610-2, and 610-3, respectively. Scatter radiation 612-1, 612-2, and 612-3, having strength s1, s2, and s3, respectively, all fall on detection point 614-1, which makes discrimination of the radiation from any individual object element difficult, if not impossible.

FIG. 6B depicts a schematic diagram of x-ray imaging system 600 with an included pinhole mask. System 616 includes system 600 and pinhole mask 618.

Pinhole mask 618 includes pinhole 620, which formed in a material suitable for blocking the passage of x-ray radiation.

Pinhole mask 618 enables independent detection of scatter radiation 612-1 at detector 608 by allowing passage of scatter radiation 612-1 through pinhole 616-1 but blocking scatter radiation 612-2 and 612-3. As a result, by making a measurement of the irradiance detected at detection point 614-1, the strength, s1, of scatter radiation 612-1 can be directly determined.

By making a second measurement of the irradiance detected at detection point 614-1 with pinhole mask 618 positioned so that scatter radiation 612-2 passes through pinhole 616-1 to detector 608 but scatter radiation 612-1 and 612-3 is blocked, the strength, s2, of scatter radiation 612-2 is directly measured.

Finally, by positioning pinhole mask 618 to block scatter radiation 612-1 and 612-2 and pinhole 616-1 but allow scatter radiation 612-3 to reach detector 608, a third measurement of the irradiance detected at detection point 614-1 provides a direct measurement of the strength, s3, of scatter radiation 612-3.

As a result, by making three separate measurements of the irradiance detected by detector 608, while knowing the position of pinhole mask 618 for each measurement and the position of detection point 614-1 on detector 608, the along-beam position and x-ray scatter characteristics of all object elements interrogated with pencil beam 604 can be determined.

Of course, the example depicted in FIGS. 6A and 6B shows measurement of only three object points for illustration. In reality, nearly every point along the path of pencil beam 604 generates other scattered rays at a plurality of angles. All these other scattered x-rays must be detected in order to be able to probe the structure and composition of object 606 along the entire path of pencil beam 604.

Figure 6C:
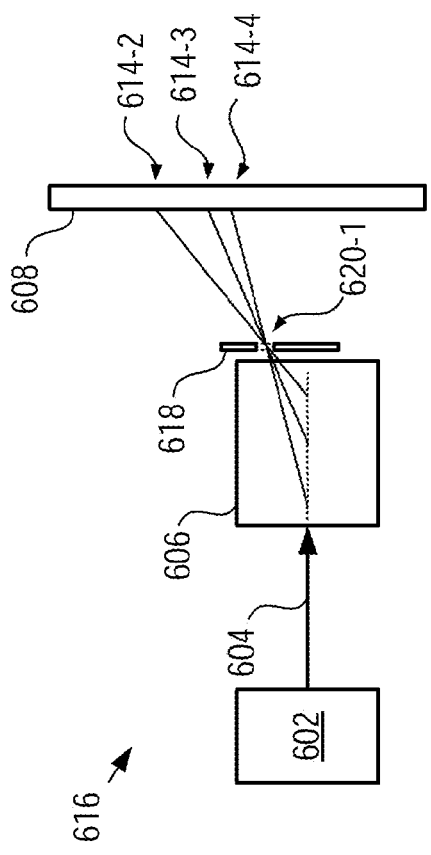
FIG. 6C depicts a schematic diagram of x-ray imaging system 616 in operation as a pinhole imaging system.

FIG. 6C depicts a schematic diagram of x-ray imaging system 616 in operation as a pinhole imaging system.

Detector 608 detects scatter radiation generated at various points along the path of pencil beam 604. This scatter radiation is scattered at angles such that all of their paths go through pinhole 620-1 and are detected at mutually distinct detection points (i.e., detection points 614-2, 614-3, and 614-4). As a result, the strengths of the x-ray radiation scattered from all object elements that passes through pinhole 620-1 can be accurately measured by detector 608 (subject to the resolution of the detector) without mutual interference and without interference from other scattered x-rays that do not go through pinhole 620-1.

A complete characterization of all the strengths of all scattered x rays can be obtained through a series of measurements with a series of pinhole masks wherein each mask has a pinhole at a different position. The size of pinhole 620-1 determines the resolution with which material is probed along the path of pencil beam 604 and also determines how many positions are required for pinhole 620-1 are needed for a complete characterization.

Each individual measurement made with pinhole 620-1 at a particular location yields values of x-ray strengths at those detection points where the path of the scatter radiation is imaged. These values represent the strengths of scatter radiation arriving at detector 608 at specific angles of incidence selected by the position of the pinhole. A complete series of measurements yields, for each point on detector 608, multiple x-ray strength values, one for each possible angle of incidence on the photographic plate. It should be noted that system 600, as depicted in FIG. 6A, provides measurements of x-ray irradiance at detector 608. In contrast, the inclusion of pinhole mask 618 converts irradiance measurement into radiance measurement by imparting angular sensitivity into their measurements. As a result, systems 616 and 622 provide a measurement of the x-ray radiance at detector 608.

One skilled in the art will recognize that each individual measurement requires that object 606 must be exposed to the x-rays for a time, T, sufficient to achieve an estimate of x-ray strength with a desired accuracy. For N measurements of object 606, therefore, the total time required for such a series is equal to N*T. For a measurement of only the strengths of scatter radiation 612-1, 612-2, and 612-3, for example, it is necessary to perform three individual measurements so the total exposure time of object 606 to x-ray radiation is 3T. It should be noted that measurement accuracy is a function of the total amount of radiation detected during a measurement. As a result, a longer exposure typically yields a more accurate measurement. As the number of measurements required increases, however, the length of time needed for an accurate measurement series can become prohibitive.

Figure 6D:
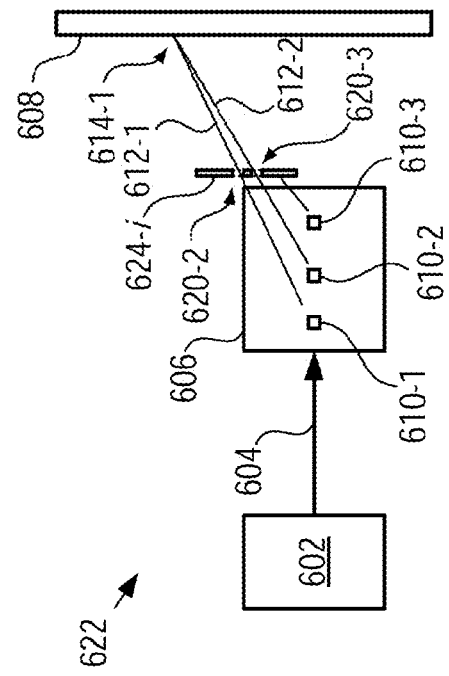
FIG. 6D depicts a schematic diagram of x-ray imaging system 600 with an included coded aperture mask.

FIG. 6D depicts a schematic diagram of x-ray imaging system 600 with an included coded aperture mask. System 622 comprises system 600 and aperture plates 624-$i$ (where $i$=1, 2, or 3). System 622 employs a simplified coded aperture mask that enables a reduction (as compared to that needed for system 616) in the total time necessary to determine the scattering characteristics of all object elements interrogated with pencil beam 604, with no loss of accuracy.

Each of aperture plates 624-$i$ is analogous to pinhole mask 618; however, each of aperture plates 624-$i$ includes two pinholes rather than one—pinholes 620-2 and 620-3.

For a first measurement, aperture plate 624-1 is used. Aperture plate 624-1 includes pinholes 616-2 and 616-3 located in the same positions as pinhole 616-1 during the first two measurements using system 616, as described above. In other words, pinholes 616-2 and 616-3 enable both of scatter radiation 612-1 and 612-2 to pass through aperture plate 624 and fall on detection point 614, while scatter radiation 612-3 is blocked. As a result, the irradiance detected at detection point 614, d3, is equal to s1+s2.

In similar fashion, for a second measurement, aperture plate 624-2 is used. Aperture plate 624-2 includes pinholes 616-2 and 616-3 located in the same positions as pinhole 616-1 during the first and third measurements using system 616, as described above. In other words, pinholes 616-2 and 616-3 enable both of scatter radiation 612-1 and 612-3 to pass through aperture plate 624 and fall on detection point 614, while scatter radiation 612-2 is blocked. As a result, the irradiance detected at detection point 614, d2, is equal to s1+s3.

Finally, for a third measurement, aperture plate 624-3 is used. Aperture plate 624-3 includes pinholes 616-2 and 616-3 located in the same positions as pinhole 616-1 during the second and third measurements using system 616, as described above. In other words, pinholes 616-2 and 616-3 enable both of scatter radiation 612-2 and 612-3 to pass through aperture plate 624 and fall on detection point 614, while scatter radiation 612-1 is blocked. As a result, the irradiance detected at detection point 614, d1, is equal to s2+s3.

The results of these three measurements can be used to compute the values of s1, s2, and s3. In particular, through some algebraic manipulations it is found that:

$$\begin{cases} s_1 = (d_2 + d_3 - d_1)/2 \\ s_2 = (d_1 + d_3 - d_2)/2 \\ s_3 = (d_1 + d_2 - d_3)/2 \end{cases} \quad (1)$$

The three measurements can be regarded as equivalent to the direct measurements of object 606 using pinhole camera system 616 in that they also yield measurements of s1, s2, and s3, albeit through mathematical manipulations of the measurement results.

As mentioned above, measurement accuracy is dependent on the total amount of radiation detected during a measurement. As a result, accuracy can also be improved by increasing the strength of the detected radiation. Since the use of aperture plates 624-i results in the combined strength of each of d1, d2, and d3 being twice that of each direct measurement of s1, s2, and s3 made using system 600, it is possible to reduce the exposure time for each measurement and still achieve comparable measurement accuracy.

One skilled in the art will recognize, however, that it is possible to drastically reduce measurement time still further by use of decompressive estimation. Each of the measurements s1, s2 and s3 is associated with a unique code position. As discussed above, compressive measurement techniques were disclosed in U.S. Pat. No. 7,616,306 and U.S. Pat. No. 8,149,400, among others. Using such techniques, it is possible to separate images taken simultaneously through a coded aperture by a combination of image priors and local code texture analysis. As a result, and in contrast to a scanned pinhole camera, acceptable image fidelity for irradiance and tomographic imaging can be achieved in as few as one time step. It is also possible to use adaptive-control coded-aperture translation and exposure to significantly reduce image acquisition time and, thus, the duration of exposure of an object to x-ray radiation.

The use of a coded aperture affords embodiments of the present advantage additional advantage with respect to measurement noise. A common type of measurement noise is additive Gaussian noise. If the same exposure time, T, is used for the measurements using pinhole mask 618 and aperture plates 624-i, both sets of measurements are characterized by the same amount of additive Gaussian noise. Those skilled in the art will recognize, however, that the estimates of s1, s2, and s3 obtained from d1, d2, and d3 through equation (1) have a noise variance that is less than the noise variance associated with the direct measurements of 51, s2, and s3 as performed using pinhole mask 618. This is because in the measurements using aperture plates 624-i, the total amount of signal detected at detector 608 is twice as much as the total amount of signal that is detected in the direct measurements using pinhole mask 618. Each of scatter radiations 612-1, 612-2, and 612-3 is measured twice using aperture plates 624-i, but only once using pinhole mask 618, which compensates for the fact that the scatter radiations are not measured individually.

In addition, nonlinear signal estimation strategies, such as are described by A. Mrozack, et al., in "Coded aperture spectroscopy with denoising through sparsity," *Optics Express*, Vol. 20, 2297-2309 (2012), which is incorporated herein by reference, enable improved signal to noise performance from multiplex-coded data even when Poisson noise is dominant. Further, the use of decompressive inference and adaptive, image-based, measurement enables real-time allocation of measurement-integration time to significantly improve the fidelity of a reconstructed image.

Returning now to FIGS. 2-3, at operation 306, processor 226 employs a longitudinal forward model to reconstruct the composition of object 110 in region 212-i-j to classify and locate any objects along axis 112. Processor 226 reconstructs the composition of region 212-i-j by estimating its coherent scatter properties based on output signal 224, which is based on modulated image 234 (e.g., as manifested in plots 500, 502, and/or 504), the shape and intensity of pencil beam 208, and the aperture pattern of coded aperture 218. In some embodiments, spectral filters are included in system 200, thereby enabling processor 226 to further characterize object 110 based on its spectral characteristics.

The irradiance detected at detector 222 yields the vector $g_m = I(r_m)$, where $r_m$ is the center of the $m^{th}$ pixel of the detector, and $I(r)$ is the measured irradiance at the $m^{th}$ pixel.

Employing a planar transmission function to model coded aperture 218, assuming that pencil beam 208 can be modeled as a single ray along axis 112, a computational longitudinal forward model of object 110 can be built by expanding the scattering density $F(z,k,\theta)$ over a discrete set of voxel basis functions $\Phi(z,q)$ (taken to be rectangular in z and q), as:

$$F(z) = \int \Sigma f_n \Phi_n(z,q) dq \quad (2)$$

a transformation of the integration variables to (z,q) yields a discrete forward model of the matrix equation g=Hf, where the object vector f has components $f_n$ and the matrix H is a "forward matrix" having components:

$$H_{mn} = \int \frac{dz'}{z} \left(\frac{\cos\theta}{2\sin\frac{\theta}{2}}\right)^2 t_2\left(r_m\left[1 - \frac{z_1}{z'}\right]\right) \int q\,dq\,S\left(\frac{q}{2\sin\frac{\theta}{2}}\right)\Phi_n(z',q) \quad (3)$$

and where the scattering angle θ is represented by:

$$\theta = \cos^{-1}(z'/\sqrt{r^2_m + z'^2}) \quad (4)$$

An approximate inverse of the matrix H can be computed using numerical methods for the measurements depicted in FIG. 5.

Given a vector, f, of object coefficients as defined by equation (2) above, the irradiance measured by each pixel is given in discrete form by Hf, provided above as g=Hf. Since images 500, 502, and 504 also contain background contributions with mean $\mu_b$, the actual measurements, y, are approximated by the Poisson process as $$y \sim \text{Poisson}(Hf + \mu_b) \quad (5)$$

where Poisson(v) is a vector of independent Poisson observations with mean intensities given by the components of v. Given y, H, and a noisy realization of the background b~Poisson($\mu_b$), it is an aspect of the present invention that an accurate estimation of f can be obtained by estimating $\mu_b$ from b using a Poisson image denoising algorithm and using the resulting estimate, $\mu'_b$, of $\mu_b$ to reconstruct f. The estimate of $\mu'_b$ is obtained using a maximum penalized likelihood estimation method, which provides:

$$\mu'_b = \mathrm{argmin}_{g \in \Gamma}(-\log P(b|g) + \tau pen(g)), \quad (6)$$

where the Poisson likelihood P(b|g) is given by:

$$P(b|g) = \prod_i P(b_i | g_i) = \prod_i \frac{\exp(-g_i) g_i^{bi}}{b_i!}, \quad (7)$$

and where i indexes pixel 230, $\Gamma$ is a collection of possible estimates to search from, pen(g) is the penalization or the regularization function corresponding to estimate g, and $\tau$ is the term that balances the log-likelihood term and the penalization term.

In an algorithm in accordance with the present invention, a multiscale, partition-based estimate is chosen that is the best fit to the data and also is piecewise smooth. The penalization term is proportional to the number of cells in the partition and is enforces the assumption that $\mu_b$ is piecewise smooth.

Using $\mu'_b$, an estimate of f is made according to a generalize maximum likelihood (GML) estimator given by:

$$\hat{f} = \mathrm{argmin}_f(-\log P(y|H, \hat{\mu}_b, \tilde{f})), \quad (8)$$

where the GML estimate of f is obtained using a Richardson-Lucy iterative deconvolution method, as described by W. H. Richardson in "Bayesion-based iterative method of image restoration," in the *Journal of the Optical Society of America*, Vol. 62, pp. 55-59 (1972), which is incorporated herein by reference.

In addition to the modulation induced by coded aperture 218, the diffraction patterns shown in FIG. 5 comprise concentric rings, which can be represented over bins in the polar coordinates ($\rho$, $\phi$). For the purposes of this Specification, including the appended claims, the term "polar downsampling" is defined as representing a diffraction pattern over bins in polar coordinates. It is yet another aspect of the present invention that this polar downsampling can significantly decrease the computational complexity of an algorithm used to reconstruct region 212-*i-j*. This affords embodiments of the present invention advantages over the prior art. Some of the advantages gained by polar downsampling can be evaluated by calculating the number of ) and ) bins needed for an effective reconstruction of the region. As discussed above, and with respect to FIG. 2, detector 222 is approximately 40 cm×30 cm. The radius values of the concentric rings shown in FIG. 5 are within the range of 0-25 cm. The intersection of pencil beam 208 with the detector plane (i.e., at z=0) defines 233 radius bins between $\rho$=2.5 cm and $\rho$=11.5 cm. The polar angle was similarly segmented over its entire range into 120 bins. As a result, embodiments of the present invention enable a reduction in the required sampling from 2048×1536 to 233×120, significantly simplifying the computation of H.

FIGS. 7A-D depict reconstruction results for a sample interrogated by an x-ray pencil beam in accordance with the illustrative embodiment of the present invention. The results depicted in these figures are based on a forward matrix H for the pencil beam system that was calculated by sampling region 212-*i-j* using rectangular voxels with widths of ⅓ cm in z and 0.3 rad/nm in q. From plots 500, 502, and 504, the coefficient vector f representing the scattering density F(z,q) of the region was estimated using the methods described above.

FIG. 7A depicts a spatial scattering profile for a first test sample interrogated by a pencil beam of x-ray radiation. Plot 700 shows the spatial scattering profile, F(z), for a sodium chloride sample as a function of distance, z, from detector 218, with the sample placed at a distance of 60.2 cm from the detector (i.e., z=60.2 cm).

FIG. 7B depicts a spatial scattering profile for a second test sample interrogated by the pencil beam of x-ray radiation. Plot 702 shows the spatial scattering profile for an aluminum sample as a function of distance, z, from detector 218, with the sample placed at z=60.2 cm.

In each case, the beam penetrated only 1 cm of each sample; however, the spatial extent of the reconstructed objects has a FWHM of about 3 cm. The reconstructions depicted in each of plots 702 and 704 are approximately centered at the true object positions, demonstrating the along-beam ranging capability of system 200.

FIG. 7C depicts a momentum transfer profile for the first test sample. Plot 704 shows the momentum transfer profile, F(q), for the sodium chloride sample as a function of distance, z, from detector 218.

FIG. 7D depicts a momentum transfer profile for the second test sample. Plot 706 shows the momentum transfer profile, F(q), for the aluminum sample as a function of distance, z, from detector 218.

The scattering density F(z,q) determined from plots 700 and 702 was integrated over a 3 cm region around the expected object position to yield a momentum transfer profile F(q)=F(z,q)dz. Aside from an overall scaling, the exact width of this window was determined to have a minimal effect on the integrated profile. The reconstructed profiles (solid) are shown along with the reference data (dashed) in FIGS. 7C and 7D, respectively, and all plots are normalized to have a maximum value of unity. The two dominant peaks for each material are reconstructed with the correct locations and approximate relative intensities, however reconstruction of the smaller peaks is frustrated by noise in the acquired diffraction patterns. The FWHM of the dominant reconstructed peaks is approximately 1.6 rad/nm.

FIG. 8A depicts a spatial scattering profile for both the first and second test sample simultaneously interrogated by a pencil beam of x-ray radiation. Plot 800 shows the spatial scattering profile, F(z), for a sodium chloride sample and aluminum sample as a function of distance, z, from detector 218, with the sodium chloride sample placed at a distance of 59.3 cm from the detector and the aluminum sample placed at a distance of 52 cm from the detector.

FIG. 8B depicts a momentum transfer profile for the first of two test samples simultaneously interrogated by a pencil beam of x-ray radiation. Plot 802 shows the momentum transfer profile, F(q), for the sodium chloride sample as a function of distance, z, from detector 218.

FIG. 8C depicts a momentum transfer profile for the second of two test samples simultaneously interrogated by a pencil beam of x-ray radiation. Plot 804 shows the momentum transfer profile, F(q), for the aluminum sample as a function of distance, z, from detector 218.

From the results shown in FIGS. 7A-D and 8A-C, it can be seen that system 200 has significant utility for estimating the elastic scattering structure of target samples. Further, by enabling differentiation of x-rays arriving on detector elements 230 from multiple directions, the present invention enables improved photon efficiency over scatter imaging systems of the prior art.

At operation 307, stage 232 moves object 110 to index the location of pencil beam on object 110. Once pencil beam has been indexed to the next image point 210-*i-j*, operations 303 through 306 are repeated to characterize new region 212-*i-j*.

Stage 232 is a conventional three-axis stage suitable for moving object 110 through all of regions 212.

At operation 308, volumetric estimate 228 is generated based on the collection of characterizations of regions 212-*i-j*.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. A system for providing an image of a region of an object, the region including a plurality of object elements, and the region defining a longitudinal axis, the system comprising:
    a source of radiation operable for interrogating the object with a first radiation signal having energy within an energy passband that ranges from approximately 30 keV to approximately 69.5 keV;
    a coded aperture operable for modulating a second radiation signal received from the object, the second radiation signal being based on the first radiation signal;
    a detector comprising a two-dimensional arrangement of pixels, the detector operable for detecting a modulated image based on the modulated second signal; and
    a processor operable for computing an estimate of the composition of the region based on the modulated image and a longitudinal forward model of the system.

2. The system of claim 1 wherein the second radiation signal comprises x-ray radiation scattered by at least one of the plurality of object elements.

3. The system of claim 1 wherein the source is operable for providing the first radiation signal such that it is substantially collimated.

4. The system of claim 1 wherein the source is operable for providing the first radiation signal such that it is substantially fan-shaped.

5. The system of claim 1 wherein the source is operable for providing the first radiation signal such that it is substantially cone-shaped.

6. The system of claim 1 wherein the second radiation signal comprises a fluorescent signal from at least one of the plurality of object elements.

7. The system of claim 1 wherein the coded aperture is operable for modulating the second radiation signal with a periodic function.

8. The system of claim 7 wherein the processor is further operable for demodulating the modulated image to determine the position along the longitudinal axis of at least one of the plurality of object elements.

9. The system of claim 1 wherein the coded aperture comprises an arrangement of apertures that modulates the second radiation signal with a scale-dependent code.

10. The system of claim 9 wherein the processor is further operable for demodulating the scale-dependent code to determine the position along the longitudinal axis of at least one of the plurality of object elements.

11. The system of claim 1 wherein the processor is further operable for processing the modulated image to compute a scatter spectrum for each of at least two of the plurality of object elements.

12. The system of claim 1 wherein the processor is further operable for (1) processing the modulated image to estimate a momentum transfer profile for at least one of the plurality of object elements and (2) determining the composition of the at least one of the plurality of object elements.

13. The system of claim 1, wherein the processor is further operable for computing the estimate based on polar down-sampling.

14. The system of claim 1 wherein the coded aperture is radially symmetric about a center point.

15. The system of claim 1 wherein the coded aperture is radially asymmetric about a center point.

16. The system of claim 1 wherein the coded aperture comprises a plurality of apertures that is in an arrangement that collectively defines a periodic code, and wherein the processor is further operable to independently estimate (1) object density and (2) scatter angle versus position along the longitudinal axis for the plurality of object elements based on the periodic code.

17. A method for estimating the composition of a region of an object, the region including a plurality of object elements, and the region defining a longitudinal axis, the method comprising:
    interrogating the region with an input signal comprising x-ray radiation having an energy within an energy passband that ranges from approximately 30 keV to approximately 69.5 keV;
    providing a first radiation signal by encoding radiance information on a second radiation signal from the plurality of object elements, wherein the second radiation signal is based on the input signal;
    receiving a modulated image at a detector comprising a plurality of irradiance pixels, the modulated image being based on the first radiation signal;
    providing an output signal from the detector, the output signal being based on the modulated image; and
    computing an estimate of (1) the position along the longitudinal axis and (2) the scatter properties of each of the plurality of object elements based on the output signal and a longitudinal forward model of the system.

18. The method of claim 17 wherein the second radiation signal comprises energy of the input signal scattered by object elements in the region.

19. The method of claim 17 further comprising providing the second radiation signal by stimulating fluorescence at each of the plurality of object points.

20. The method of claim 17 wherein the first radiation signal is encoded by modulating the second radiation signal with a coded aperture that is dimensioned and arranged to modulate the second radiation signal with a periodic function.

21. The method of claim 20 further comprising demodulating the modulated image to determine the position along the longitudinal axis of at least one of the plurality of object elements.

22. The method of claim 17 wherein the first radiation signal is encoded by modulating the second radiation signal with a coded aperture having a plurality of apertures, the plurality of apertures being dimensioned and arranged to modulate the second radiation signal with a scale-dependent code.

23. The method of claim 22 further comprising demodulating the scale-dependent code to determine the position along the longitudinal axis of at least one of the plurality of object elements.

24. The method of claim 17 wherein the radiance information is encoded on the second radiation signal by modulating it with a coded aperture that includes a plurality of apertures arranged in an arrangement that is periodic in at least one dimension.

25. The method of claim 17 wherein the radiance information is encoded on the second radiation signal by modulating it with a coded aperture that includes a plurality of apertures are arranged in an arrangement that is radially symmetric about a center point.

26. The method of claim 17 wherein the radiance information is encoded on the second radiation signal by modulating it with a coded aperture that includes a plurality of apertures are arranged in an arrangement that is radially asymmetric about a center point.

27. The method of claim 17 wherein the estimate of the scatter properties of each of the plurality of object elements is computed based on polar downsampling.

28. The method of claim 17 further comprising:
  processing the modulated image to estimate a momentum transfer profile for at least one of the plurality of object elements; and
  determining the composition of the at least one of the plurality of object elements.

29. The method of claim 17 further comprising:
  providing a coded aperture comprising a plurality of apertures that is in an arrangement that collectively defines a periodic code, wherein the radiance information is encoded on the second radiation signal via the coded aperture;
  estimating object density for the plurality of object elements based on the periodic code; and
  estimating scatter angle versus position along the longitudinal axis for the plurality of object elements based on the periodic code;
  wherein the estimate of object density is made independently of the estimate of scatter angel versus position.

* * * * *